United States Patent
Alumbaugh

(10) Patent No.: US 10,513,677 B2
(45) Date of Patent: Dec. 24, 2019

(54) RECESSED ROOF FOR A STORAGE TANK

(71) Applicant: T.F. Warren Group Corporation, Spring, TX (US)

(72) Inventor: Billy Ray Alumbaugh, Goodman, MO (US)

(73) Assignee: TF Warren Group Corporation, Spring, TX (US)

( * ) Notice: Subject to any disclaimer, the term of this patent is extended or adjusted under 35 U.S.C. 154(b) by 0 days.

(21) Appl. No.: 15/901,382

(22) Filed: Feb. 21, 2018

(65) Prior Publication Data
US 2018/0237735 A1 Aug. 23, 2018

Related U.S. Application Data

(60) Provisional application No. 62/461,582, filed on Feb. 21, 2017.

(51) Int. Cl.
*E04B 7/02* (2006.01)
*E04H 7/06* (2006.01)
(Continued)

(52) U.S. Cl.
CPC .............. *C12M 21/04* (2013.01); *C02F 3/28* (2013.01); *C12M 23/02* (2013.01); *C12M 23/36* (2013.01);
(Continued)

(58) Field of Classification Search
CPC ...... C12M 21/04; C12M 23/38; C12M 23/36; C12M 41/40; C12M 41/00; C12M 23/02;
(Continued)

(56) References Cited

U.S. PATENT DOCUMENTS

| | | | | | |
|---|---|---|---|---|---|
| 1,392,197 | A | * | 9/1921 | Wall | C02F 3/28 210/603 |
| 1,717,100 | A | * | 6/1929 | Downes | C02F 3/28 210/603 |
| 1,904,339 | A | * | 4/1933 | Wiggins | B65D 88/34 220/227 |

(Continued)

OTHER PUBLICATIONS

"Organic Liquid Storage Tanks," Chapter 7, Section 1 of AP 42, Fifth Edition, vol. 1 published by the Environmental Protection Agency in Nov. 2006.

(Continued)

*Primary Examiner* — Fred Prince
(74) *Attorney, Agent, or Firm* — C. Tumey Law Group PLLC

(57) ABSTRACT

This disclosure may generally relate to a pressured vessel and, more particularly, to systems and methods for pressurizing a pressured vessel by producing a biogas using a recessed roof system. A pressured vessel may comprise a shell, wherein the shell may comprise a plurality of panels. The pressured vessel may further comprise a recessed roof and a deck. A method of collecting biogas from a pressure vessel may comprise disposing a liquid into the pressure vessel, disposing an anaerobic microorganism into the pressure vessel, adjusting a path of the biogas with a protruding baffle, collecting the biogas with the recessed roof, applying pressure to the outside of the recessed roof with the liquid such that the biogas pressure inside the recessed roof is increased, and removing the biogas from inside the recessed roof through a gas collection system.

20 Claims, 2 Drawing Sheets

(51) Int. Cl.
*C02F 3/28* (2006.01)
*C12M 1/107* (2006.01)
*C12M 1/00* (2006.01)
*C12M 1/34* (2006.01)

(52) U.S. Cl.
CPC ............ *C12M 23/38* (2013.01); *C12M 41/00* (2013.01); *C12M 41/40* (2013.01); *C12M 47/10* (2013.01); *E04B 7/022* (2013.01); *E04H 7/065* (2013.01); *Y02E 50/343* (2013.01)

(58) Field of Classification Search
CPC . C12M 47/10; C02F 3/28; C02F 11/04; E04B 7/022; E04H 7/065; Y02E 50/343
USPC .............................................. 210/603; 71/10
See application file for complete search history.

(56) References Cited

U.S. PATENT DOCUMENTS

| | | | | |
|---|---|---|---|---|
| 2,538,412 | A | * | 1/1951 | Cecil .................... C02F 3/2873 126/360.2 |
| 2,907,712 | A | * | 10/1959 | Eidsness .................. C02F 3/28 210/194 |
| 3,228,295 | A | * | 1/1966 | Kane ........................ F41A 9/20 89/1.802 |
| 8,409,439 | B1 | | 4/2013 | Tovani et al. |
| 2006/0076291 | A1 | * | 4/2006 | Wells ....................... C02F 3/28 210/603 |

OTHER PUBLICATIONS

"Complete Storage & Cover Solutions for Anaerobic Digesters," published by CST Storage in 2015.

* cited by examiner

RECESSED ROOF FOR A STORAGE TANK

CROSS-REFERENCE TO RELATED APPLICATIONS

The present application claims priority to U.S. Provisional Application No. 62/461,582, filed Feb. 21, 2017, the entire disclosure of which is incorporated herein by reference.

BACKGROUND

Currently, storage tanks may be pressurized and act as a pressured vessel. Often, storage tanks may be pressurized to hold a fluid at a pressure substantially different from the atmospheric pressure. Due to internal pressures, there may be structural issues in how a roof of the storage tank may connect to the body of the storage tank and prevent joint leakage. These problems may be due to the relatively thin metal and connection angles between the roof and the storage tank body. This may cause the connection point to fail, releasing the pressure within the storage tank and further preventing the storage tank from being pressurized.

Storage tanks may be pressurized for any number of operations and for any variety of function. For example, in an operation a storage tank may be used to collect biogas. It may be desirable to use a storage tank to produce and collect a biogas. Different industries may produce biodegradable waste as a by-product of operations. It may be beneficial to utilize a storage tank as an anaerobic/aerobic digester to convert the produced biodegradable waste into a useful biogas. To move the biogas from the storage tank to another area for processing, the storage tank is often pressurized with expensive equipment and systems. Current designs and requirements of storage tanks may inhibit the implementation of the storage tank as an anaerobic/aerobic digester. The cost of equipment necessary to facilitate the safety and control of pressurizing a vessel may prevent the ability to produce a biogas in regions around the world. Thus, storage tank capable of collecting biogas and being pressurized without costly equipment may be desirable.

BRIEF DESCRIPTION OF THE DRAWINGS

These drawings illustrate certain aspects of some of the embodiments of the present invention and should not be used to limit or define the invention.

DETAILED DESCRIPTION

Embodiments relate generally to a pressurized storage tank. More particularly, embodiments relate to a recessed roof that may be used to pressurize and prevent failure between the storage tank wall and the recessed roof. In embodiments, the combination of the recessed roof and the storage tank may be utilized to collect a biogas produced within the storage tank. Advantageously, the recessed roof disclosed herein may reduce the cost and labor associated with pressurizing the storage tank. Additionally, a recessed roof may negate the need for additional pneumatic equipment that may be necessary to increase the pressure in a pressurized vessel, which may be expensive. The disclosed invention may implement gravity and utilize hydrostatic pressure to increase the pressure within the storage tank.

Figure 1:
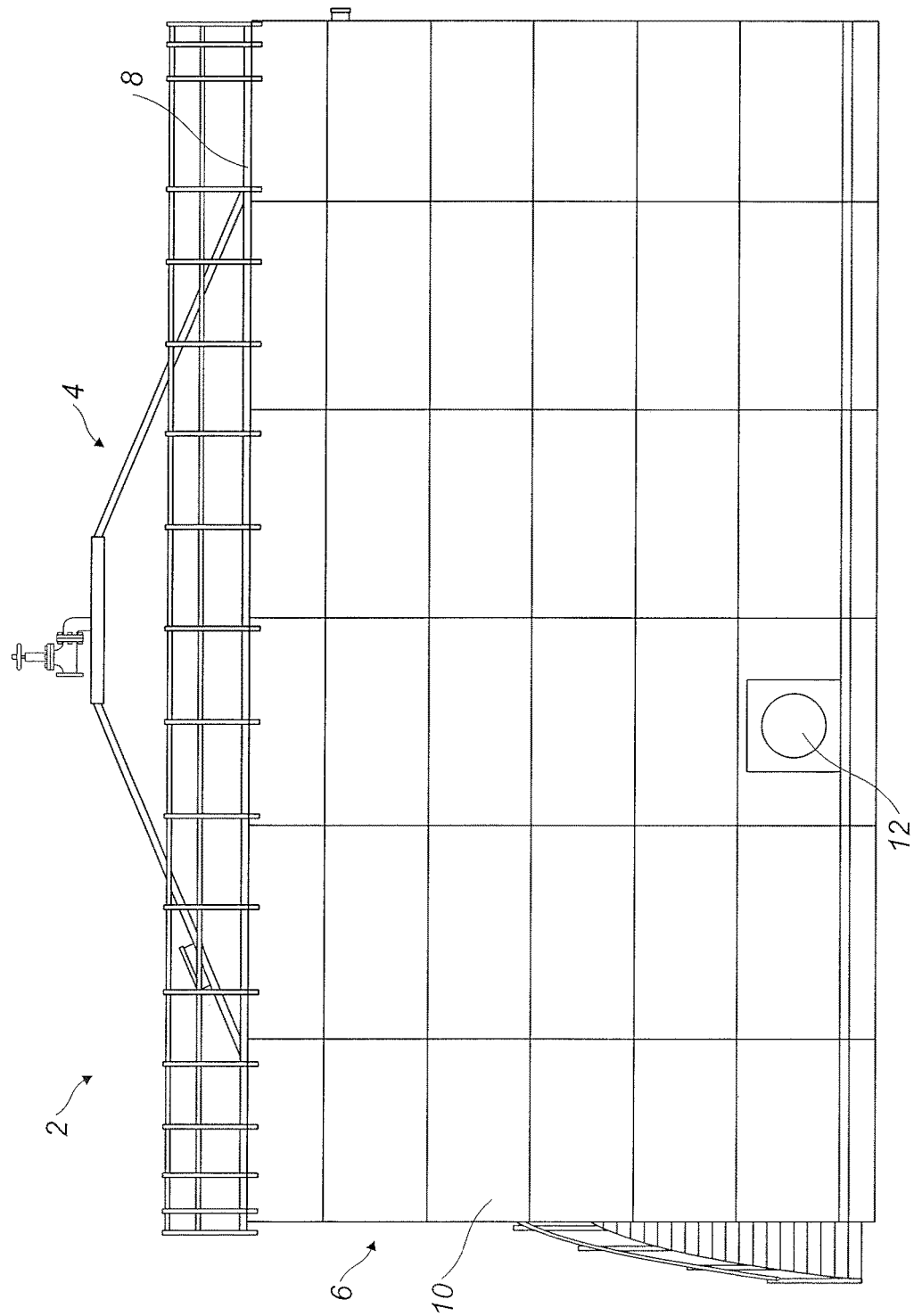
FIG. 1 illustrates a side perspective view of a storage tank.

FIG. 1 illustrates an embodiment of a pressured vessel 2. Pressured vessel 2 may be any suitable size, height, and/or shape. In embodiments, pressured vessel 2 may comprise a recessed roof 4, a shell 6, and a deck 8. Shell 6 may form the body of pressured vessel 2 and may provide structural support to pressured vessel 2. In embodiments, shell 6 may be in the shape of a hollow cylinder. Shell 6 may be formed from a plurality of panels 10.

As illustrated, there may be a plurality of panels 10 which may be constructed together to form shell 6. Panels 10 may be any suitable size, height, and/or shape. Without limitation, a suitable shape may include, but is not limited to, a cross-sectional shape that is circular, elliptical, triangular, rectangular, square, hexagonal, and/or combinations thereof. In some embodiments, panels 10 may be rectangular. Panels 10 may comprise any suitable material to withstand pressure exerted upon them. In embodiments, suitable material may include metals, plastic, rubber, neoprene, composites or any combination thereof. In some embodiments, suitable material may be, but is not limited to, stainless steel, aluminum, carbon steel, black iron, and/or any combination thereof. In embodiments, each panel 10 may comprise the same and/or different suitable material in comparison to another panel 10. For example, panels 10 near the bottom of pressured vessel 2 may be made of a stronger material due to the potential fluid pressure that may be exerted on pressured vessel 2 would be larger at such a location. Panels 10 near the top of pressured vessel 2 may be made of a resistant metal, such as stainless steel, in comparison to the bottom of pressured vessel 2. Additionally, the thickness of each panel 10 may vary as the height of pressured vessel 2 increases. For example, the panels 10 near the bottom may be thicker to better structurally support a filled pressure vessel whereas the panels 10 near the top may be thinner.

It should be noted that panels 10 may be connected to each other using any suitable mechanism, including, but not limited, through the use of suitable fasteners, threading, adhesives, welding and/or any combination thereof. Without limitation, suitable fasteners may include nuts and bolts, washers, screws, pins, sockets, rods and studs, hinges and/or any combination thereof. Additionally, sealants, gaskets, and the like may be used between connection points between panels 10. A plurality of panels 10 may be attached to form a row and rows may be stacked to form shell 6. Formed, shell 6 may comprise an inner surface and an outer surface. The outer surface may be defined as the exterior surface exposed to outside elements. The inner surface may be defined as the internal surface and may be exposed to fluids and/or gases disposed in pressured vessel 2. Shell 6 may further comprise an inlet 12. Inlet 12 may be disposed at any suitable location on shell 6. Inlet 12 may allow for fluids and products to be disposed internally in shell 6. During operations, an operator may displace any suitable substance through inlet 12 and into pressured vessel 2. An operator may be defined as an individual, group of individuals, or an organization. Inlet 12 may be any suitable size, height, and/or shape. Without limitation, a suitable shape may include, but is not limited to, a cross-sectional shape that is circular, elliptical, triangular, rectangular, square, hexagonal, and/or combinations thereof. As illustrated, inlet 12 may be circular and may connect to a piping system (not illustrated). Shell 6, may further form a structural base for recessed roof 4.

Recessed roof 4 may provide a cost-efficient way to pressurize pressured vessel 2. Recessed roof 4 may be disposed about the top of shell 6. As further discussed below, recessed roof 4 may attach at or near the top of shell 6, for example, within ten feet of the top of shell 6. In alternative embodiments recessed roof 4 may attach to inner surface of shell 6 within about five feet to about ten feet, about ten feet to about fifty feet, about twenty-five to about seventy-five feet, about thirty feet to about forty feet, about one foot, or about fifteen feet of the top of shell 6. In embodiments, recessed roof 4 may be utilized to collect biogas. Additionally, utilizing hydrostatic pressure, recessed roof 4 may be pressurized to facilitate the movement of collected biogas from recessed roof 4 to an offsite location for use and/or a refinement center. A fluid may be disposed on at least a portion of recessed roof 4, which may apply hydrostatic force to the top of recessed roof 4. Deck 8 may be disposed about the top of shell 6 to protect the fluid disposed on at least a portion of recessed roof 4 from outside elements. Without limitation, deck 8 may attach to shell 6 and recessed roof 4 to form a water tight barrier. Deck 8 may attach to shell 6 and recessed roof 4 through any suitable mechanism, including, but not limited, through the use of suitable fasteners, threading, adhesives, welding and/or any combination thereof. Without limitation, suitable fasteners may include nuts and bolts, washers, screws, pins, sockets, rods and studs, hinges and/or any combination thereof. Deck 8 may be able to support an operator who uses deck 8 to access recessed roof 4. Deck 8 may allow for operators to access the top of pressured vessel 2 and treat, maintain, remove, and/or add elements stored and/or present within pressured vessel 2. Additionally, decking 8 may comprise openings, ports, and/or railing for safety requirements.

Figure 2:
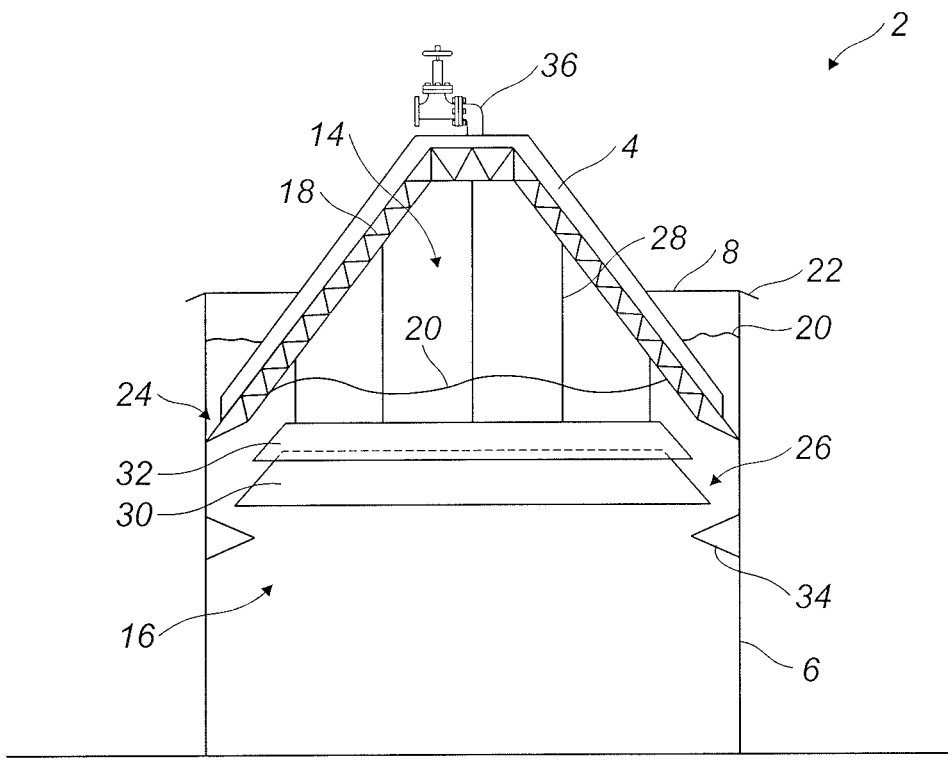
FIG. 2 illustrates a cut away view of a storage tank with a recessed roof.

FIG. 2 illustrates an embodiment of a pressured vessel 2 with a recessed roof 4. During operations, pressured vessel 2 may serve as a container for anaerobic digestion to produce biogas. Typically, during anaerobic digestion microorganisms may break down biodegradable material in the absence of oxygen to produce a biogas. In embodiments, the biogas may include carbon dioxide, methane, and/or combinations thereof. The biogas may subsequently be collected and used in other applications. As illustrated in FIG. 2, recessed roof 4 may be constructed to collect biogas 14 from a liquid 16. Liquid 16 may comprise, but is not limited to, water, biodegradable feedstocks, wastewater, sewage, fluids related to the oil and gas industry, and/or combinations thereof. Biogas 14 may be produced and separated from liquid 16 during operation within pressured vessel 2. In operations, biogas 14 may be separated, collected, and transferred for other uses. Additionally, processed liquid 16, liquid 16 free of biogas 14 and free of other contaminants may be collected for additional use outside of pressured vessel 2.

To collect biogas 14, recessed roof 4 may be constructed to withstand hydrostatic pressure exerted upon it to pressurize pressured vessel 2. As illustrated, recessed roof 4 may be structurally supported by rafters 18. In embodiments, rafters 18 may connect recessed roof 4 to pressured vessel 2. Rafters 18 may be any suitable size, height, and/or shape. Without limitation, a suitable shape may include, but is not limited to, a cross-sectional shape that is circular, elliptical, triangular, rectangular, square, hexagonal, and/or combinations thereof. In some embodiments, rafters 18 may be elongated beams. Rafters 18 may be connected together to form any suitable framework of supporting structure members (i.e., a truss). The suitable framework may be open, or have sections along the framework that are open, to allow material to pass through. Rafters 18 may be connected to each other through the use of suitable fasteners. Without limitation, suitable fasteners may include nuts and bolts, washers, screws, pins, sockets, rods and studs, hinges and/or any combination thereof. Rafters 18 may comprise any suitable material for supporting recessed roof 4 and to resist corrosion from liquid 16. In embodiments, suitable material may include metals, plastic, rubber, neoprene, composites or any combination thereof. In particular embodiments, suitable material may be, but is not limited to, stainless steel, aluminum, steel, black iron, and/or any combination thereof.

Without limitation, rafters 18 may be disposed above and/or below a water line 20 of liquid 16. Water line 20 may be defined as the surface of liquid 16. As illustrated, rafters 18 may connect to an inner surface of shell 6 below top ledge 22 of shell 6. Without limitation, there may be any number of rafters 18 that may be spaced no more than thirty inches apart. A suitable range for the spacing between rafters 18 may be from about one inch to about ten inches, from about ten inches to about twenty inches, or from about twenty inches to about thirty inches. In alternative embodiments, rafters 18 a spacing over thirty inches may be between each rafter 18. Rafters 18 may function as the structural support for recessed roof 4, which may allow for recessed roof 4 to capture biogas 14.

In embodiments, at least a portion of recessed roof 4 may be disposed underneath water line 20 in liquid 16. Recessed roof 4 may comprise any material that may prevent liquid 16 or gas 14 from escaping pressured vessel 2. Suitable materials may be, but are not limited to, metal, plastic, cloth, and/or any combination thereof. In embodiments, suitable materials may include factory-coated carbon steel, stainless steel, and/or combinations thereof. In embodiments, recessed roof 4 may be any suitable size, height, and/or shape. Without limitation, a suitable shape may include, but is not limited to, a cross-sectional shape that is circular, elliptical, triangular, rectangular, square, hexagonal, and/or combinations thereof. In some embodiments, recessed roof 4 may be in a similar shape as rafters 18 as to accommodate being disposed on top of or underneath rafters 18. In alternative embodiments, recessed roof 4 may be disposed underneath rafters 18. It should be noted that recessed roof 4 may not be in contact with panels 10. For examples, as illustrated in FIG. 2, recessed roof 4 may attach to rafters 18 and rafters 18 may be attached to an inner surface of shell 6. The separation between recessed roof 4 and the inner surface of shell 6 may form corridor 24.

Corridor 24 may allow liquid 16, which may be free of contaminants and/or gas 14, to move from below recessed roof 4 to above recessed roof 4. As illustrated in FIG. 2, water line 20 may be disposed above at least a portion of recessed roof 4 and rafters 18. Liquid disposed above recessed roof 4 may apply hydrostatic pressure to recessed roof 4. This may increase the pressure below recessed roof 4, which may allow an operator to remove biogas 14 from pressured vessel 2 without expensive equipment. Without limitation, corridor 24 may generally range from about two inches to about six inches between the inner surface of shell 6 and recessed roof 4. Without limitation, corridor 24 may be from about two inches to about three inches, from about three inches to about four inches, from about four inches, to about five inches, or from about five inches to about six inches. In embodiments, corridor 24 may further comprise at least a portion of rafters 18 as rafters 18 may not hinder the flow of liquid 16 from under recessed roof 4, through corridor 24, to above recessed roof 4. Thus, as operations commence, there may be a hydrostatic force acting on the exterior of recessed roof 4 to equalize the internal pressure acting within pressured areas of the vessel 2, specifically under recessed roof 4.

During operations, pressured vessel 2 may function to displace fluid 16, which may increase pressure under recessed roof 4. For example, liquid 16, which may comprise water, biodegradable feedstocks, wastewater, sewage, fluids related to the oil and gas industry may be introduced into pressured vessel 2 through inlet 12 (e.g. Referring to FIG. 1). Liquid 16 may be forced to rise as biogas 14 accumulates within liquid 16. Biogas 14 may form as a byproduct from the anaerobic/aerobic digester. As illustrated in FIG. 2, pressured vessel 2 may comprise at least one baffle 26. During operations, as liquid 16 rises with biogas 14, biogas 14 may encounter baffles 26. Baffles 26 may direct the flow of biogas 14, disposed in liquid 16, to an area below recessed roof 4. In embodiments, baffles 26 may be any suitable size, height, and/or shape. Without limitation, a suitable shape may include, but is not limited to, a cross-sectional shape that is circular, elliptical, triangular, rectangular, square, hexagonal, and/or combinations thereof. In some embodiments, baffles 26 may have a cross-sectional shape that is a hollow circle. The diameter of baffles 26 may decrease as the height of baffles 26 increases (i.e., the height may be sloped). In embodiments, the shape of baffles 26 may be similar to the shape of pressured vessel 2.

For example, if pressured vessel 2 is cylindrical, baffles 26 may have a hollow, circular cross-section. If pressured vessel 2 is cubic, baffles 26 may have a hollow, square cross-section. Baffles 26 may comprise any suitable material that is resistant to corrosion from liquid 16. In embodiments, suitable material may include metals, plastic, rubber, neoprene, composites or any combination thereof. Without limitation, at least a portion of baffles 26 may attach to an inner surface of shell 6 at any suitable location and/or may be suspended from rafters 18. In embodiments, baffles 26 may be suspended from rafters 18 by support cables/structural members 28. Support cables 28 may be any suitable means in which an object is subjected to hanging. Suitable means may include wire, chains, cable, structural steel and/or the like. Without limitation, baffles 26 may be supported by braces (not illustrated) attached to the floor of pressured vessel 2 (e.g. Referring to FIG. 1) and extending upwards.

Baffles 26 may be arranged in any suitable fashion in relation to each other. For example, a first baffle 30 may be disposed within pressured vessel 2 at about the midpoint of the height of pressured vessel 2, and a second baffle 32 may be disposed within pressured vessel 2 at a position above first baffle 26. Second baffle 26 may be concentric, staggered, and/or offset from first baffle 26. In embodiments, baffles 26 may operate to transport biogas 14 towards the area underneath recessed roof 4. During operations, biogas 14 may accumulate in liquid 16. As a given volume in liquid 16 increases with biogas 14, that mixture may start to rise throughout pressured vessel 2. Baffles 26 may direct the mixture of liquid 16 and biogas 14 towards the water line 20 underneath recessed roof 4 and prevent biogas 14 from moving through corridor 24. In additional embodiments, biogas 14 may accumulate in the area underneath recessed roof 4 and may provide internal pressure within pressured vessel 2 to provide pressurization for the process of producing a liquid 16, which may be later clean and collected.

Additionally, a protruding baffle 34 disposed on the inner surface of pressured vessel 2. Protruding baffle 34 may serve to direct the flow of biogas 14 away from the inner surface of shell 6. Without limitation, protruding baffle 34 may attach to the inner surface of shell 6 at any suitable height within pressured vessel 2. Protruding baffle 34 may attach to the inner surface of pressured vessel 2 through any suitable mechanism, including, but not limited to, through the use of suitable fasteners, adhesives, welding and/or any combination thereof. Without limitation, suitable fasteners may include nuts and bolts, washers, screws, pins, sockets, rods and studs, hinges and/or any combination thereof protruding baffle 34 may be the initial barrier that liquid 16 comprising biogas 14 may encounter as liquid 16 and biogas 14 rise throughout pressured vessel 2. Protruding baffle 34 may direct the flow of liquid 16 towards baffles 26. In embodiments, protruding baffle 34 may be any suitable size, height, and/or shape. Without limitation, a suitable shape may include, but is not limited to, a cross-sectional shape that is circular, elliptical, triangular, rectangular, square, hexagonal, and/or combinations thereof. In some embodiments, protruding baffle 34 may have a cross-sectional shape that is a hollow circle. The diameter of baffles 26 may decrease and/or increase as the height of protruding baffle 34 increases (i.e., the height may slope). Protruding baffle 34 may comprise any suitable material that is resistant to corrosion from liquid 16. In embodiments, suitable material may include coated or uncoated metals, plastic, rubber, neoprene, composites or any combination thereof.

It should be noted that as liquid 16 rises, biodegradable feedstocks, wastewater, sewage, fluids related to the oil and gas industry that may be disposed in liquid 16 may also rise to water line 20. However, the biodegradable feedstocks, wastewater, sewage, fluids related to the oil and gas industry may sink after rising to water line 20. As the biodegradable feedstocks, wastewater, sewage, fluids related to the oil and gas industry sinks, it may encounter baffles 26 and protruding baffle 34. To prevent biodegradable feedstocks, wastewater, sewage, fluids related to the oil and gas industry from accumulating and/or becoming stuck on baffles 26 and/or protruding baffle 34, both baffles 26 and/or protruding baffles 34 may comprise downward slope. This may allow the biodegradable feedstocks, wastewater, sewage, fluids related to the oil and gas industry to slide of both baffles 26 and/or protruding baffles 34 to the bottom of pressured vessel 2 to undergo further transformation by the anaerobic/aerobic digester. Likewise both baffles 26 and/or protruding baffles 34 may comprise an upward slope that may help direct biogas 14 to the area below recessed roof 4.

As biogas 14 collects under recessed roof 4 the pressure may increase and force liquid 16 under recessed roof 4 to recede as liquid 16 is displaced. The displaced liquid 16 may travel through corridor 24 and rises above recessed roof 4. Liquid 16 disposed upon recessed roof 4 may provide a "head" for hydrostatic pressure to pressurize the area below recessed roof 4. In embodiments, recessed roof 4 may further include a gas collection system 36. Gas collection system 36 may comprise any number of suitable number of valves and pipes to remove biogas 14 from pressured vessel 2. As the area below recessed roof 4 is pressurized, an operator may only actuate a valve within gas collection system 36 and the pressure from pressured vessel 2 may move biogas 14 through gas collection system 36, without additional equipment. It should be noted that over pressure protection is provided in area above liquid 16 disposed on recessed roof 4 and between deck 8. Furthermore deck 8 may comprise vents (not illustrated) that may allow for over pressure to vent into the atmosphere. This over pressure protection is passive and may eliminate the need to use a more complicated and expensive pressure relief valve or system.

Additionally, deck 8 may comprise an opening (not illustrated) in which an operator may be able to remove liquid 16 that is disposed above recessed roof 4. As liquid 16 in this area may be relatively clean, liquid 16 may be removed from pressured vessel 2 and undergo further treatment prior to use in other applications.

Figure 3:
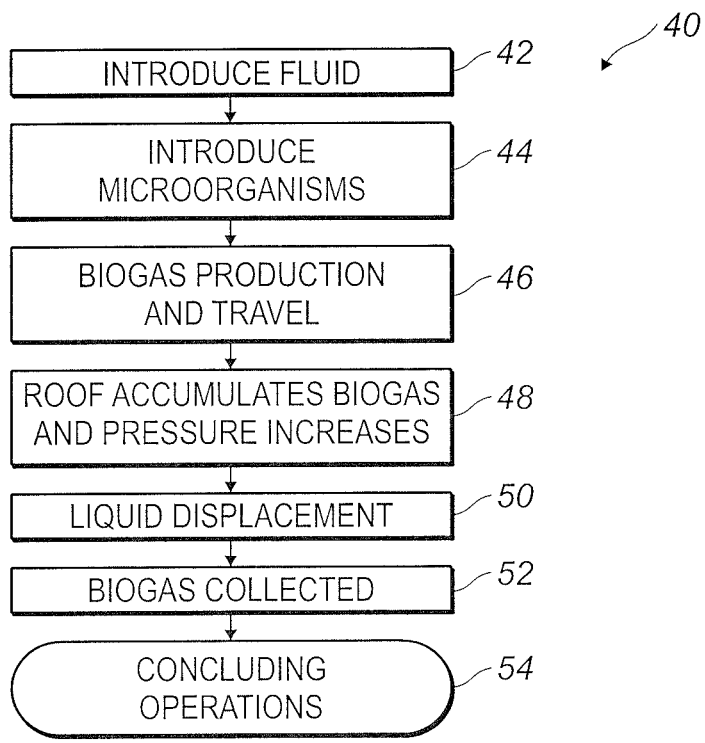
FIG. 3 illustrates a flowchart depicting a biogas collection method.

FIG. 3 illustrates a flowchart depicting a biogas collection method 40, utilizing recessed roof 4 (e.g., referring to FIG. 2). Collecting biogas 14 may begin with the initial step 42 of introducing a fluid into pressured vessel 2 (e.g., referring to FIG. 2). For example, liquid 16 may be pumped into and/or disposed within pressured vessel 2 through inlet 12 (e.g., referring to FIG. 1). Liquid 16 may be contaminated with solid contaminants, such as, but is not limited to, biodegradable feedstocks, wastewater, sewage, fluids related to the oil and gas industry, and/or combinations thereof. Contaminates disposed in liquid 16 may be broken down by an aerobic/aerobic digester.

In step 44, a microorganism (not illustrated) may be introduced into pressured vessel 2. In embodiments, anaerobic/aerobic microorganisms may be disposed into pressured vessel 2 through inlet 12 and/or through any other available ports or openings in pressured vessel 2. The anaerobic/aerobic microorganisms may break down the solid contaminants disposed in liquid 16. There may be a plurality of factors that affect the rate in which the anaerobic/aerobic microorganisms may break down the solid contaminants. Without limitation, some factors may be the temperature within pressured vessel 2, the solid content of the solid contaminants, batch or continuous processes, and/or the like. A byproduct produced by the anaerobic/aerobic microorganisms as it breaks down the solid contaminants is biogas 14.

In step 46, biogas 14 is produced by the anaerobic/aerobic microorganisms and travels upward to water line 20 within pressured vessel 2. As previously described, biogas 14 may be any suitable biogas including, but not limited to, carbon dioxide and/or methane. As the amount of solid contaminants decreases and the amount of biogas 14 may increases, liquid 16 may decrease in unit weight. Gas within liquid 16 may start to float towards the top of pressured vessel 2 and to water line 20 (e.g., referring to FIG. 2). As liquid 16 changes, remaining solid particles may settle from liquid 16 to the bottom of pressured vessel 2, which may be due to gravity. Without limitation, baffles 26 and/or protruding baffle 34 (e.g., referring to FIG. 2) may be sloped in a desirable fashion as to allow the solid particles to travel to the bottom of vessel 2. In embodiments, as biogas 14 within the liquid 16 moves toward the top of vessel 2, biogas 14 within liquid 16 may combine to form bubbles (not illustrated). Biogas 14 may be directed by baffles 26 and/or protruding baffle 34 toward the center of pressured vessel 2. In alternate embodiments, biogas 14 may be directed to any other suitable location wherein biogas 14 may encounter water line 20 underneath recessed roof 4. In embodiments, biogas 14 may move through any type of maze, labyrinth, obstacles, and/or the like to ensure biogas 14 is moved to the desired location of pressured vessel 2.

In step 48, biogas 14 may accumulate under recessed roof 4, which may increase the pressure under recessed roof 4. As biogas 14 approaches water line 20, biogas 14 may leave liquid 16 and accumulate into the air above water line 20 underneath recessed roof 4. In embodiments, biogas 14 may be trapped between water line 20 and recessed roof 4 due to the differences in material density. As biogas 14 accumulates under recessed roof 4, biogas 14 may increase the pressure which may displace water line 20 downward.

In step 50, liquid 16 may be displaced as a result of increasing the content of biogas 14 underneath recessed roof 4. As pressured vessel 2 is pressurized, it may force liquid 16, free of solid contaminants and gas through corridor 24 (e.g., referring to FIG. 2). Moving through corridor 24, liquid 16 may be disposed on recessed roof 4. In embodiments, liquid 16 above recessed roof 4 may apply hydrostatic force downward due to the increasing weight of liquid 16 on top of recessed roof 4. The hydrostatic pressure above the recessed roof 4 and biogas 14 pressure will equalize and provide motive force to pressurize biogas 14.

In step 52, biogas 14 may be collected from underneath recessed roof 4. In embodiments, an operator may collect and remove biogas 14 from pressured vessel 2 by opening gas collection system 36, attached to submerged roof 4, which may direct biogas 14 to a desired location through gas collection system 36 for further use. Additionally, bio gas 14 may be monitored to maintain a constant pressure within pressured vessel 2. After the desired amount of bio gas 14 is collected, a concluding step 54 may be implemented in biogas collection method 40.

Concluding step 48 may comprise of various clean-up processes. Liquid 16 disposed above recessed roof 4 may be collected for further use outside of pressured vessel 2. The remaining liquid 16 may be pumped out of pressured vessel 2. Lastly, the solid contaminants that had separated from liquid 16 may be cleaned out of pressured vessel 2.

In alternative embodiments, recessed roofing 4 may be implemented in retro-fitting pressure vessels 2, which may have previously been built. For example, a roof (not illustrated), may be removed from a previously built pressured vessel 2. Once the roof has been removed, an operator may dispose rafters 18 within pressured vessel 2, which may connect to an inner surface of shell 6 below the top most edge of shell 6. Rafters 18 may be disposed within pressured vessel 2 from a crane and/or fabricated in place by an operator on scaffolding and/or lifts. Additionally, baffles 26 and/or protruding baffle 34 may be attached to the inner surface of shell 6 and/or disposed below rafters 18. Recessed roof 4 may then be disposed on rafters 18. Recessed roof 4 may be disposed for example, from about two inches to about six inches from the inner surface of shell 6 which may form corridor 24. Deck 8 may be attached to top ledge 22 and recessed roof 4, preventing external contaminates from entering pressured vessel 2. Liquid 16 may be pumped into retro-fitted pressured vessel 2 to begin the process of producing biogas 14.

The foregoing figures and discussion are not intended to include all features of the present techniques to accommodate a buyer or seller, or to describe the system, nor is such figures and discussion limiting but exemplary and in the spirit of the present techniques.

What is claimed is:

1. A pressured vessel, comprising:
   a shell, wherein the shell comprises:
   a plurality of panels; and
   a recessed roof; and
   a deck, configured to protect a fluid disposed on at least a portion of the recessed roof.

2. The pressured vessel of claim 1, wherein the recessed roof is attached to an inner surface of the shell.

3. The pressured vessel of claim 2, wherein the recessed roof is supported by a plurality of rafters and wherein the plurality of rafters are attached to the inner surface of the shell.

4. The pressured vessel of claim 1, further comprising a corridor, wherein the corridor is a gap between the recessed roof and an inner surface.

5. The pressured vessel of claim 4, further comprising a gas collection system, wherein the gas collection system is disposed on the recessed roof.

6. The pressured vessel of claim 1, further comprising a protruding baffle, wherein the protruding baffle is dispose on an inner surface of the shell.

7. The pressured vessel of claim 6, wherein the protruding baffle comprises a downward slope and an upward slope.

8. The pressured vessel of claim 1, further comprising a protruding baffle and at least one baffle.

9. The pressured vessel of claim 8, wherein the at least one baffle is supported on an inner surface of shell 6 or suspended from the recessed roof.

10. The pressured vessel of claim 9, wherein the at least one baffle comprises a downward slope and an upward slope.

11. A method of collecting biogas from a pressure vessel, comprising:
    disposing a liquid into the pressure vessel, wherein the liquid comprises:
    biodegradable material that is disposed at a bottom of the pressure vessel and wherein the pressure vessel comprises: a shell;
    a recessed roof; and a deck;
    disposing an anaerobic microorganism into the pressure vessel such that the anaerobic microorganism breaks down the biodegradable material and releases the biogas; adjusting a path of the biogas with a protruding baffle;
    collecting the biogas with the recessed roof such that the liquid inside the recessed roof is disposed through a corridor and onto the outside of the recessed roof, wherein the corridor is disposed between an inner surface of the shell and the recessed roof;
    applying pressure to the outside of the recessed roof with the liquid such that the biogas pressure inside the recessed roof is increased; and
    removing the biogas from inside the recessed roof through a gas collection system.

12. The method of claim 11, wherein the recessed roof is supported by rafters and wherein the rafters attach the recessed roof to the inner surface of the shell.

13. The method of claim 11, further comprising adjusting the path of the biogas with at least one baffle, wherein the at least one baffle is supported on an inner surface of shell 6 or suspended from the recessed roof.

14. The method of claim 13, wherein the at least one baffle and the protruding baffle have an upward slope and a downward slope.

15. The method of claim 11, wherein the gas collection system is disposed on the recessed roof.

16. A method of building a pressure vessel comprising:
    attaching a plurality of panels to form a shell, wherein the shell comprises an inner surface and an outer surface;
    attaching a recessed roof to the inner surface of the shell;
    forming a corridor between the recessed roof and the inner surface of the shell;
    attaching a deck, wherein the deck attaches to the top of the shell and the recessed roof, and wherein the deck is configured to protect a fluid disposed on at least a portion of the recessed roof.

17. The method of claim 16, further comprising attaching a protruding baffle to the inner surface of the shell, wherein the protruding baffle comprises a downward slope and an upward slope.

18. The method of claim 16, further comprising suspending a baffle from the recessed roof, wherein the baffle comprise a downward slope and an upward slope.

19. The method of claim 18, wherein the pressure vessel comprises a plurality of baffles.

20. The method of claim 16, attaching a gas collection system to the recessed roof.

* * * * *